United States Patent [19]

Schwan

[11] 4,041,035

[45] Aug. 9, 1977

[54] 1-BENZYL-1,2-DIHYDRO-3-METHYL-2-OXOPYRIMIDINIUM IODIDE

[75] Inventor: Thomas J. Schwan, Norwich, N.Y.

[73] Assignee: Morton-Norwich Products, Inc., Norwick, N.Y.

[21] Appl. No.: 693,934

[22] Filed: June 8, 1976

[51] Int. Cl.$^2$ .............................................. C07D 239/22
[52] U.S. Cl. ................................. 260/251 R; 424/251
[58] Field of Search ..................................... 260/251 R

[56] References Cited

U.S. PATENT DOCUMENTS

| | | | |
|---|---|---|---|
| 3,330,640 | 7/1967 | Luckenbaugh | 260/251 R |
| 3,551,425 | 12/1970 | Petersen et al. | 260/251 R |

OTHER PUBLICATIONS

Brown, "The Pyrimidines", (1962) pp. 359-361.

*Primary Examiner*—Delbert R. Phillips
*Attorney, Agent, or Firm*—Anthony J. Franze

[57] ABSTRACT

A compound 1-benzyl-1,2-dihydro-3-methyl-2-oxopyrimidinium iodide possesses pharmacological activity as an antihypertensive agent.

1 Claim, No Drawings

1-BENZYL-1,2-DIHYDRO-3-METHYL-2-OXOPYRIMIDINIUM IODIDE

This invention relates to a chemical compound. In particular, it is concerned with a compound of the formula:

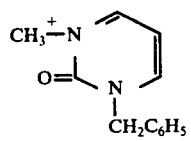

When administered intravenously to animals this compound exhibits antihypertensive activity. Administration of 50 mg/kg of this compound to anesthetized dogs caused marked inhibition of the response to epinephrine.

In order that this invention be readily available to and understood by those skilled in the art the following illustrative example is supplied: A solution of 1-benzyl-2(1H)pyrimidone, (28.1 g., 0.15 mole) in 290 ml of methanol was stirred at room temperature with 290 ml of iodomethane for 90 hours. The solution was concentrated to dryness in vacuo leaving a semi-solid which was crystallized by trituration with ethanol to give 46 g. (94%) of 1-benzyl-1,2-dihydro-3-methyl-2-oxopyrimidinium iodide.

An analytical sample, m.p. 170°-172°, was prepared from ethanol.

Anal. Calcd. for $C_{12}H_{13}IN_2O$: C, 43.92; H, 3.99; H, 8.54; Found: C, 44.06; H, 4.02; N, 8.46.

What is claimed is:

1. A compound of the formula:

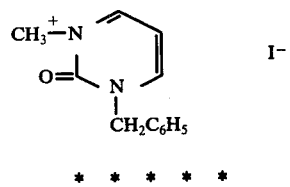

* * * * *